United States Patent
Neergaard

(10) Patent No.: US 10,485,247 B2
(45) Date of Patent: *Nov. 26, 2019

(54) CHEWING GUM COMPRISING NICOTINE

(71) Applicant: Fertin Pharma A/S, Vejle (DK)

(72) Inventor: Jesper Neergaard, Aabenraa (DK)

(73) Assignee: Fertin Pharma A/S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/766,710

(22) PCT Filed: Oct. 7, 2015

(86) PCT No.: PCT/DK2015/050299
§ 371 (c)(1),
(2) Date: Apr. 6, 2018

(87) PCT Pub. No.: WO2017/059858
PCT Pub. Date: Apr. 13, 2017

(65) Prior Publication Data
US 2018/0295856 A1 Oct. 18, 2018

(51) Int. Cl.
*A23G 4/12* (2006.01)
*A23G 4/08* (2006.01)
*A61K 9/68* (2006.01)
*A61K 9/14* (2006.01)
*A61K 31/465* (2006.01)

(52) U.S. Cl.
CPC ............ *A23G 4/12* (2013.01); *A23G 4/08* (2013.01); *A61K 9/0058* (2013.01); *A23V 2002/00* (2013.01); *A23V 2250/51084* (2013.01); *A61K 9/146* (2013.01); *A61K 31/465* (2013.01)

(58) Field of Classification Search
None
See application file for complete search history.

(56) References Cited

U.S. PATENT DOCUMENTS

| 2007/0042079 A1* | 2/2007 | Miladinov | A23G 4/066 426/5 |
| 2008/0241314 A1 | 10/2008 | Hoegl et al. | |
| 2009/0196834 A1* | 8/2009 | Andersen | A23G 4/068 424/48 |
| 2010/0260690 A1* | 10/2010 | Kristensen | A61K 9/0058 424/48 |
| 2013/0071515 A1* | 3/2013 | Wimmer | A23G 4/08 426/4 |
| 2013/0309352 A1 | 11/2013 | Wimmer et al. | |

FOREIGN PATENT DOCUMENTS

| WO | 2004056363 A2 | 7/2004 |
| WO | 2006000232 A1 | 5/2006 |
| WO | 2007104574 A2 | 9/2007 |
| WO | 2009037319 A2 | 3/2009 |
| WO | 2010121619 A1 | 10/2010 |
| WO | 2015154780 A1 | 10/2015 |

OTHER PUBLICATIONS

Wacker Vinnapas® B30 Special Vinyl Acetate Homopolymer Datasheet; downloaded Sep. 22, 2019 from http://www.matweb.com/search/DataSheet.aspx?MatGUID=7148396d817343f685837b1d1c8361c5 (Year: 2019).*
Wacker Vinnapas® B 500/20 VL Vinylactate Copolymer , downloaded Sep. 22, 2019 from http://www.matweb.com/search/DataSheet.aspx?MatGUID=2f2717c805004ce5ad3b567332e6d048 (Year: 2019).*

* cited by examiner

*Primary Examiner* — Michael P Cohen
(74) *Attorney, Agent, or Firm* — St. Onge Steward Johnston & Reens LLC

(57) ABSTRACT

A nicotine chewing gum is disclosed, the nicotine chewing gum having gum base polymers, nicotine, and microcrystalline cellulose as a carrier for the nicotine, the gum base polymers include polyvinyl acetate and vinyl laurate-vinyl acetate copolymer in an amount of more than 90% by weight of the gum base polymers, and the gum base polymers include 20-95% by weight of polyvinyl acetate and 5-80% by weight of vinyl laurate-vinyl acetate copolymer. Also, a method for producing a nicotine chewing gum is disclosed.

21 Claims, 1 Drawing Sheet

CHEWING GUM COMPRISING NICOTINE

FIELD OF THE INVENTION

The invention relates to a nicotine chewing gum. The invention furthermore relates to a method of producing a nicotine chewing gum.

BACKGROUND OF THE INVENTION

One challenge of chewing gum in general is that the chewing gum is a complex delivery vehicle. Chewing gum or gum base ingredients may affect multiple properties of the chewing gum. One such example may be that the application of a particular gum base or chewing gum ingredient softens the chewing gum, thereby leading to an increased release of nicotine due to the eased chewing of the chewing gum. This may be attractive or non-attractive, but a challenge is that the release of nicotine may be different from the release of nicotine induced by another ingredient and most of all, the chewing gum texture may simultaneously be affected to a degree that the chewing gum does not have the desired typical textural chewing gum properties. This may e.g. be counteracted by the incorporation of another chewing gum ingredient making the chewing gum harder and/or increasing the elasticity, but this may then affect the desired release of nicotine and so forth. When referring to typical textural chewing gum properties, it is here noted that the desired rheology of chewing gum is very different from the rheology of typical chewy confectionery such as toffee, chocolate, wine gum, etc. This is in particular the case in relation to the elastic properties required to obtain a confectionery product satisfying the consumer's expectations in relation to a chewing gum.

A particular challenge in relation to nicotine chewing gum is that the nicotine released may cause an unpleasant sensory sensation for the user of the chewing gum which is generally referred to as burning. On the other hand there is a desire to maximize the nicotine release from the chewing gum, as it is this nicotine which provides the user of the chewing gum the desired counteraction of craving.

In other words, the nicotine should be released, but at the same time the nicotine released causes the burning.

One possible way of increasing the amount of nicotine delivered to the body of the person chewing a nicotine chewing gum is increasing the amount of nicotine in the nicotine chewing gum. Several drawbacks may, however, be associated with this approach, such as increased burning due to a resulting increased release of nicotine. Moreover, nicotine is a relatively expensive substance, and increasing the amount of nicotine in a nicotine chewing gum may therefore increase the manufacturing costs of such nicotine chewing gums.

SUMMARY OF THE INVENTION

The invention relates to a nicotine chewing gum comprising gum base polymers, nicotine, and microcrystalline cellulose as a carrier for the nicotine, the gum base polymers comprising polyvinyl acetate and vinyl laurate-vinyl acetate copolymer in an amount of more than 90% by weight of the gum base polymers, and wherein the gum base polymers include 20-95% by weight of polyvinyl acetate and 5-80% by weight of vinyl laurate-vinyl acetate copolymer.

One very important advantage of the present invention may be that a relatively high release of the nicotine may be obtained without causing too much discomfort for the user of the nicotine chewing gum. This may otherwise be a problem for nicotine chewing gums, which may often cause considerable discomfort in the form of a burning sensation (also referred to as "burning" or "nicotine burning") for the users. However, by the present invention, release of nicotine may be increased while maintaining a relatively constant level of burning. The burning may in some cases be lowered by decreasing the release of nicotine; however, it is often a very important feature for a nicotine chewing gum that it may have a relatively high release of nicotine in order to imitate the smoking of a cigarette, thus alleviating the craving a smoker may often feel.

One further advantage of the invention may be that by including microcrystalline cellulose as a carrier for the nicotine, the nicotine is immobilized in a manner such that it may be kept relatively isolated from the chewing gum ingredients other than the microcrystalline cellulose itself. However, the nicotine should not just be bound inside the nicotine chewing gum not to be released, but released in a timely manner, already in the oral cavity when the nicotine chewing gum is chewed, in order to secure the intended release and also subsequent uptake into the body of the nicotine.

A still further advantage of the invention may be that a very effective immobilization of nicotine may be obtained for nicotine at the free base form without the use of e.g. the conventional polacrilex ion exchange resin, while still obtaining relatively high release of nicotine. Thus, the use of buffering agent may in some cases be avoided or at least reduced while maintaining an effective uptake of nicotine into the body since the nicotine may be provided on the free base form due to the use of cellulose as carrier. Thus, the invention may provide for an effective craving relief due to effective release of nicotine and effective uptake of nicotine.

According to the provisions of the invention it may be possible to obtain a nicotine chewing gum which may even release more nicotine than conventional nicotine chewing gums and without causing an increase of the so-called burning sensation.

It is even more noted that the burning sensation may be comparable to conventional nicotine chewing gum even when conventional chewing gum releases nicotine significantly slower than the inventive chewing gum.

According to an embodiment of the invention, it is possible to omit polyterpene resins, resins based on gum rosin, wood rosin or tall oil resin in the nicotine chewing gum or gum base formulation. It is thereby possible to obtain a reproducible chewing gum without affecting the release of e.g. nicotine substantially. It is therefore possible to apply chewing gums and gum bases for their intended purposes without significantly changing the properties of the nicotine chewing gum or gum base when natural resins are omitted.

According to an advantageous embodiment of the invention an attractive texture may be obtained by the application of synthetic gum base polymers while retaining an acceptable release of nicotine. It should in particular be noted that the application of synthetic gum base polymers without any application of polyterpene resins or resins based on gum rosin, wood rosin or tall oil resin provides an attractive base for nicotine.

In an embodiment of the invention, the chewing gum exhibits several very advantageous properties such as improved texture and improved release of nicotine.

Improved texture according to an embodiment of the invention may be obtained through sufficient elastic properties of the applied gum base polymer blend to resemble a conventional chewing gum feel.

The improved release of nicotine according to an embodiment of the invention may be obtained through the fact that the synthetic gum base polymers are able to release the nicotine in a way still facilitating a relatively high degree of taste masking by means of sweeteners and flavors.

Furthermore, the chewing gum of the invention may exhibit less variation with respect to release of nicotine, when compared to conventional nicotine chewing gum.

One very significant advantage of the invention may be that nicotine may be delivered to the oral cavity by means of the very attractive claimed chewing gum platform with reduced burning sensation in the oral cavity for the user.

In the context of the present invention it should be understood that microcrystalline cellulose as carrier for the nicotine may be referred to as carrier cellulose or microcrystalline carrier cellulose. Thus, carrier cellulose and microcrystalline carrier cellulose is to be distinguished from e.g. cellulose as a filler. In some preferred embodiments, the carrier cellulose and the nicotine is mixed together before being added to and/or mixed with the gum base polymers. Also, when referring to "microcrystalline cellulose", microcrystalline cellulose as carrier for the nicotine is generally meant, unless specifically otherwise stated.

According to an advantageous embodiment of the invention said nicotine is nicotine in its base form.

It should be understood in connection with the above embodiment that the nicotine chewing gum may in some embodiments comprise an active ingredient in addition to nicotine. Such further active ingredient may comprise further nicotine, which is not the free base form of nicotine, but instead nicotine provided e.g. as a salt or as a complex with an ion exchange resin, such as nicotine polacrilex. However, in other embodiments all of the included nicotine in the nicotine chewing gum is provided on free base form.

According to the above embodiment, the nicotine in the nicotine chewing gum is the free base form of nicotine bound to the microcrystalline cellulose, e.g. by means of adsorption or absorption.

According to an embodiment of the invention, the nicotine is added to the nicotine chewing gum as free base form of nicotine. For example, the nicotine may be bound to cellulose, e.g. by adsorption or absorption.

It should be understood in connection with the above embodiment that the nicotine chewing gum may in some embodiments comprise further cellulose, which is not microcrystalline cellulose; this may e.g. be cellulose as filler. However, in other embodiments, all the cellulose of the nicotine chewing gum is microcrystalline cellulose.

One advantage of the above embodiment may be that microcrystalline cellulose may absorb a relatively high amount of nicotine, while also allowing for the nicotine to be effectively released from the nicotine chewing gum when chewed.

According to an advantageous embodiment of the invention the total content of gum base ingredients selected from the list consisting of polyterpene resins, resins based on gum rosin, wood rosin and tall oil resin is less than 5 percent by weight of the nicotine chewing gum, such as less than 3 percent by weight of the nicotine chewing gum, such as less than 2 percent by weight of the nicotine chewing gum, such as less than 1 percent by weight of the nicotine chewing gum, such as less than 0.5 percent by weight of the nicotine chewing gum, such as less than 0.2 percent by weight of the nicotine chewing gum.

For example the total content of polyterpene resins, resins based on gum rosin, wood rosin and tall oil resin is 0 percent by weight of the nicotine chewing gum, i.e. the nicotine chewing gum contains no polyterpene resins and no resins based on gum rosin, wood rosin or tall oil resin.

According to an advantageous embodiment of the invention the nicotine chewing gum contains no polyterpene resins and no resins based on gum rosin, wood rosin or tall oil resin.

According to an advantageous embodiment of the invention the nicotine chewing gum comprises gum base polymers in an amount of between 15 and 80 percent by weight of the nicotine chewing gum, such as between 20 and 60 percent by weight of the nicotine chewing gum, such as between 25 and 40 percent by weight of the nicotine chewing gum.

According to various example embodiments, nicotine chewing gum comprises gum base polymers in an amount of about 35, about 40, or about 45 percent by weight of the nicotine chewing gum.

According to an advantageous embodiment of the invention said microcrystalline cellulose is provided in the form of particles having an average particle size between 10 and 250 micrometers.

According to an advantageous embodiment of the invention the nicotine chewing gum is substantially free of buffering agents.

A buffering agent of a nicotine chewing gum in the present context is characterized by maintaining the pH level within certain relatively constant pH values in the oral cavity. Using the free base form of nicotine may, however, at least in some cases, make the use of buffer superfluous, or decrease the need of buffer.

Reducing or eliminating the buffering agent may often lead to improvements in the taste of the nicotine chewing gum, as some users may feel that the buffering agent induces off taste in the nicotine chewing gum.

However, in other embodiments, the nicotine chewing gum comprises a buffering agent.

According to an advantageous embodiment of the invention the nicotine chewing gum comprises buffer.

According to an advantageous embodiment of the invention the buffer is present in an amount of 0.5 to 5% by weight of the nicotine chewing gum, such as 1 to 4%, such as 2 to 5%, such as 3 to 5%, such as 3 to 4%, such as 1 to 3%.

According to an advantageous embodiment of the invention the buffer is selected from the group consisting of a carbonate, including bicarbonate or sesquicarbonate, glycerinate, phosphate, glycerophosphate, acetate, glyconate or citrate of an alkali metal, such as potassium or sodium, e.g. trisodium and tripotassium citrate, or ammonium, tris buffer, amino acids, and mixtures thereof.

According to an advantageous embodiment of the invention the buffer comprises sodium carbonate, sodium bicarbonate or any combination thereof.

The buffer may to some extent be microencapsulated or otherwise coated as granules with polymers and/or lipids being less soluble in saliva than is the one or more buffering agents. Such microencapsulation controls the dissolution rate whereby the time frame of the buffering effect is extended.

In an embodiment of the invention, the nicotine chewing gum comprises a water insoluble gum base and a water soluble bulk portion, wherein the gum base and the bulk portion is mixed to form a final chewing gum core, and wherein the gum base is buffered before mixing with the bulk portion, and the buffered gum base comprises buffer from 2 to 20% by weight of the gum base before mixing with the bulk portion, such as 2 to 10%, such as 3 to 8%, such as 4 to 8%, such as 5 to 8%, such as 2 to 15%, such as 4 to 15%, such as 4 to 12%.

In an embodiment of the invention, the buffer comprises sodium carbonate, sodium bicarbonate or potassium carbonate.

According to a preferred embodiment of the invention, the buffer comprises sodium carbonate. The use of this buffer together with the stated polyvinyl acetate and vinyl laurate-vinyl acetate copolymer facilitates an advantageous release of buffer matching the released nicotine, while at the same time obtaining a robust chewing gum which is not dissolved by the buffer.

In an embodiment of the invention, the nicotine chewing gum comprises buffer in the amount of ½ to 5% by weight of the nicotine chewing gum, such as 1 to 4%, such as 2 to 5%, such as 3 to 5%, such as 3 to 4%, such as 1 to 3%.

In an embodiment of the invention, the nicotine chewing gum comprises a water insoluble gum base and a water soluble bulk portion, wherein the gum base and the bulk portion are mixed to form a final chewing gum core, and wherein the gum base is buffered before mixing with the bulk portion, and the buffered gum base comprises from 2 to 20% by weight of the gum base before mixing with the bulk portion, such as 2 to 10%, such as 3 to 8%, such as 4 to 8%, such as 5 to 8%, such as 2 to 15%, such as 4 to 15%, such as 4 to 12%.

According to an advantageous embodiment of the invention the nicotine chewing gum is free of ion-exchange resins.

According to an advantageous embodiment of the invention said chewing gum comprises between 0.5 and 8 mg of nicotine, such as between 1 and 5 mg of nicotine, such as between 2 and 4 mg of nicotine, such as between 1.5 and 3.0 mg of nicotine.

A single piece of chewing gum may typically contain 0.5-8 mg of nicotine, preferably 1-5 mg, such as 2 mg or 4 mg.

A buffer of a nicotine chewing gum in the present context is characterized by maintaining the pH level within certain relatively constant pH values. In the present context, the buffer must be matched to the nicotine.

The buffer may to some extent be microencapsulated or otherwise coated as granules with polymers and/or lipids being less soluble in saliva than is the one or more buffering agents. Such microencapsulation controls the dissolution rate thereby extending the time frame of the buffering effect. In order to increase the buffering capacity, one may e.g. add further buffering agents to the nicotine chewing gum.

According to an advantageous embodiment of the invention said chewing gum comprises one or more further active ingredients.

Thus, according to the above embodiment, the nicotine chewing gum comprises nicotine as a first active ingredient, and, in addition thereto, one or more further active ingredients, such as active pharmaceutical ingredients.

According to an advantageous embodiment of the invention said chewing gum comprises one or more fillers.

According to an advantageous embodiment of the invention said one or more fillers comprise filler cellulose.

In accordance with the above embodiment, it should be understood that typical cellulose types may be used as filler cellulose. In some embodiments some or all of the filler cellulose is of the same type as some or all of the carrier cellulose.

According to an advantageous embodiment of the invention the nicotine chewing gum comprises one or more fillers including magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, and combinations thereof.

According to an embodiment of the invention the nicotine chewing gum comprises one or more fillers including magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, starch polymers, fibers and combinations thereof.

According to an advantageous embodiment of the invention the filler is calcium carbonate, talc, or combinations thereof.

According to an embodiment of the invention the filler is calcium carbonate, talc, cellulose polymers or combinations thereof.

According to an advantageous embodiment of the invention the filler is present in an amount of 5-45% by weight of the nicotine chewing gum, such as in an amount of 10-40% by weight of the nicotine chewing gum.

According to an advantageous embodiment of the invention the nicotine chewing gum is substantially free of natural resins.

According to an advantageous embodiment of the invention the gum base polymers consists of synthetic gum base polymers.

According to an advantageous embodiment of the invention the weight ratio between polyvinyl acetate and vinyl laurate-vinyl acetate copolymer is from 8:1 to 2:3.

According to an advantageous embodiment of the invention the weight ratio between polyvinyl acetate and vinyl laurate-vinyl acetate copolymer is from 5:1 to 2:3.

According to an advantageous embodiment of the invention the weight ratio between polyvinyl acetate and vinyl laurate-vinyl acetate copolymer is from 3:2 to 2:3.

According to an advantageous embodiment of the invention the weight ratio between vinyl acetate monomers of vinyl laurate-vinyl acetate copolymer and vinyl laurate monomers of vinyl laurate-vinyl acetate copolymer is less than 90:10, such as 80:20, such as 60:40.

According to an advantageous embodiment of the invention the weight-average molecular weight Mw of polyvinyl acetate is from 5,000 to 120,000, such as 5,000 to 70,000, such as 7,000 to 25,000, and the weight-average molecular weight Mw of vinyl acetate-vinyl laurate copolymer is from 80,000 to 700,000, such as 100,000 to 600,000, such as 120,000 to 250,000.

According to an advantageous embodiment of the invention the weight-average molecular weight Mw of polyvinyl acetate is from 5,000 to 120,000, such as 5,000 to 70,000, such as 7,000 to 25,000.

According to an advantageous embodiment of the invention the weight-average molecular weight Mw of vinyl acetate-vinyl laurate copolymer is from 80,000 to 700,000, such as 100,000 to 600,000, such as 120,000 to 250,000.

According to an advantageous embodiment of the invention the nicotine chewing gum comprises a plasticizer.

According to an advantageous embodiment of the invention the nicotine chewing gum comprises wax.

According to an advantageous embodiment of the invention the nicotine chewing gum comprises fat.

According to an advantageous embodiment of the invention the nicotine chewing gum comprises an emulsifier.

According to an advantageous embodiment of the invention the synthetic gum base polymers are forming part of a gum base.

According to an advantageous embodiment of the invention the gum base comprises 15-45% by weight of polyvinyl acetate, 10-30% by weight of vinyl laurate-vinyl acetate copolymers, 15-45% by weight of fillers, 5-30% by weight of waxes or fats, 1-10% by weight of plasticizers and 1-10% by weight of emulsifiers.

According to an advantageous embodiment of the invention the gum base comprises 20-35% by weight of polyvinyl acetate, 12-25% by weight of vinyl laurate-vinyl acetate copolymer, 20-30% by weight of fillers, 10-20% by weight of waxes or fats, 2-8% by weight of plasticizers and 2-8% by weight of emulsifiers.

According to an advantageous embodiment of the invention the gum base polymers further comprises one or more elastomers selected from the group consisting of styrene-butadiene copolymers (SBR), polyisobutylene, isobutylene-isoprene copolymers, polyethylene, polyurethane or any combination thereof.

The use of a supplemental elastomers selected from the group consisting of styrene-butadiene copolymers (SBR), polyisobutylene (FIB), isobutylene-isoprene copolymers (IIR or butyl rubber), polyethylene or any combination thereof has proven unexpectedly advantageous in the sense that the synthetic elastomers may assist in obtaining a less pronounced burning sensation while maintaining a high level of nicotine release According to an advantageous embodiment of the invention the gum base polymers further comprises one or more elastomers in an amount of 0.1-10% by weight, such as in an amount of 1-8% by weight, such as in an amount of 1.5-6% by weight.

According to an advantageous embodiment of the invention, the weight-average molecular weight Mw of polyisobutylene (FIB) ranges from 37,000 to 1,000,000, such as 37,000 to 110,000, such as 37,000 to 70,000.

According to an advantageous embodiment of the invention the nicotine chewing gum comprises emulsifiers in an amount of 0.1% to 25% by weight of said chewing gum, such as 1-10% by weight of said chewing gum, such as 2-8% by weight of said chewing gum.

In an embodiment of the invention, the emulsifiers are selected from the group of cyclodextrins, polyoxyethylene castor oil derivatives, polyoxyethylene alkyl ethers, macrogol alkyl ethers, block copolymers of ethylene and propylene oxides, polyoxyethylene alkyl ethers, polyoxyethylene glycols, polyoxyethylene sorbitan fatty acid esters, polyoxyethylene (20) sorbitan monostearates, polyoxyethylene (20) sorbitan monooleates, polyoxyethylene stearates, sorbitan esters, diacetyl tartaric ester of monoglycerides, lactylated monoglycerides, or any combination thereof.

According to an advantageous embodiment of the invention the emulsifiers are selected from the group of acetylated monoglycerides, mono- and/or di-glycerides of fatty acids such as glycerol monostearate, acetem, lecithines and any combination thereof.

In an embodiment of the invention, the nicotine chewing gum comprises one or more plasticizers in an amount in the range of 0.1% to 25% by weight of said chewing gum.

In an embodiment of the invention the plasticizer comprises diacetin and/or triacetin.

In an embodiment of the invention the plasticizers comprise glycerol and/or medium chain triglycerides.

A preferred plasticizer is triacetin.

A further suitable plasticizer is miglyol.

According to an advantageous embodiment of the invention the plasticizer comprises diacetin and/or triacetin.

According to an advantageous embodiment of the invention the plasticizer comprises glycerol and/or medium chain triglycerides.

According to an advantageous embodiment of the invention the waxes are selected from the group consisting of paraffin waxes, microcrystalline waxes, polyethylene waxes and natural waxes.

According to an advantageous embodiment of the invention the fats are selected from the group consisting of animal fats and vegetable fats.

Waxes and fats are used for the adjustment of the texture and for softening of the chewing gum base when preparing chewing gum bases. In connection with the present invention, any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

According to an advantageous embodiment of the invention the nicotine chewing gum comprises flavor in an amount between 0.01 and 10% by weight of the nicotine chewing gum such as in an amount between 0.01 and 5% by weight of the nicotine chewing gum.

Non-exhaustive examples of flavors suitable in embodiments of the present invention are coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, *eucalyptus*, and mint, fruit essence such as from apple, pear, peach, strawberry, apricot, raspberry, cherry, pineapple, and plum essence. The essential oils include peppermint, spearmint, menthol, *eucalyptus*, clove oil, bay oil, anise, thyme, cedar leaf oil, nutmeg, and oils of the fruits mentioned above.

According to an advantageous embodiment of the invention the nicotine chewing gum comprises high intensity sweetener.

Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside and the like, alone or in combination.

According to an advantageous embodiment of the invention the nicotine chewing gum comprises bulk sweeteners including sugar and/or sugarless components.

According to an advantageous embodiment of the invention the nicotine chewing gum comprises bulk sweetener in an amount of 5 to about 95% by weight of the nicotine chewing gum, more typically 20 to about 80% by weight, and more commonly, 30 to 60% by weight of the nicotine chewing gum.

The sweeteners often fill the role of bulking agents in the gum. The sweeteners are improving juiciness of the gum and are supporting the flavor profile of the gum.

Sugar sweeteners generally include, but are not limited to saccharide-containing components commonly known in the chewing gum art, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination.

The sweetener can be used in combination with sugarless sweeteners.

Generally, sugarless sweeteners include components with sweetening characteristics but which are devoid of the commonly known sugars and comprise, but are not limited to, sugar alcohols such as sorbitol, mannitol, xylitol, hydrogenated starch hydrolyzates, maltitol, isomalt, erythritol, lactitol and the like, alone or in combination.

According to an advantageous embodiment of the invention the synthetic gum base polymers are resin(s) and elastomer(s).

In an embodiment of the invention, the synthetic gum base polymers are forming part of the gum base.

According to an advantageous embodiment of the invention the nicotine chewing gum is free of antioxidants.

The amount of antioxidants in chewing gum according to embodiments of the invention may be reduced or antioxidants may even be avoided. This may be due to improved stability of the nicotine chewing gum with respect to oxidation.

According to an advantageous embodiment of the invention the nicotine chewing gum comprises gum base in an amount of 30-75% by weight of the nicotine chewing gum before any optionally applied coating, such as 35-70% by weight of the nicotine chewing gum or 40-65% by weight of the nicotine chewing gum or 45-60% by weight of the nicotine chewing gum.

According to an advantageous embodiment of the invention the nicotine chewing gum is manufactured in a two-step process, the first step including the process of providing gum base in a first mixing process and a further step including the process of mixing gum base with further chewing gum components in a further mixing process.

According to an advantageous embodiment of the invention the nicotine chewing gum is manufactured in a one step process by means of an extruder.

According to an advantageous embodiment of the invention said microcrystalline cellulose is provided in the form of particles having an average particle size between 15 and 200 micrometers, such as between 20 and 150 micrometers, such as between 50 and 100 micrometers, such as about 75 micrometers.

According to an advantageous embodiment of the invention said microcrystalline cellulose has a specific surface area of between 0.65 and 1.5 m$^2$/g, such as between 0.75 and 1.25 m$^2$/g, such as between 0.85 and 1.15 m$^2$/g, such as between 0.9 and 1.1 m$^2$/g, such as about 0.95 m$^2$/g, about 1.00 m$^2$/g, or such as about 1.05 m$^2$/g.

According to an advantageous embodiment of the invention said microcrystalline cellulose has a bulk density between 0.1 and 1.0 grams per cubic centimeter (g/cm$^3$), such as between 0.25 and 0.5 grams per cubic centimeter, such as between 0.26 and 0.31 grams per cubic centimeter, or such as between 0.28 and 0.33 grams per cubic centimeter.

In the context of the above embodiment it should preferably be understood that the bulk density of the microcrystalline cellulose is understood as the bulk density at about 25 degrees Celsius.

According to an advantageous embodiment of the invention said microcrystalline cellulose has a porosity characterized by an average specific pore volume between 0.003 cm$^3$/g and 0.60 cm$^3$/g, such as between 0.01 and 0.3 cm$^3$/g.

According to an advantageous embodiment of the invention said microcrystalline cellulose has a moisture content of less than about 5% by weight, such as between 2 and 5% by weight, such as between 3 and 5% by weight, such as about 4% by weight.

According to an advantageous embodiment of the invention a weight-ratio between the nicotine and the microcrystalline cellulose is between 1:1000 and 1:1, such as between 1:500 and 1:2, such as between 1:50 and 1:5.

According to an advantageous embodiment of the invention said chewing gum comprises microcrystalline cellulose in an amount of 0.1 mg to 8 mg.

According to an advantageous embodiment of the invention the microcrystalline cellulose comprises pores, the pores having an average pore size of between about 3 nanometers and about 300 nanometers, such as between 10 nanometers and 200 nanometers, such as between 20 nanometers and 100 nanometers.

According to an advantageous embodiment of the invention said microcrystalline cellulose is derived from wood pulp.

The microcrystalline cellulose according to the above embodiment is carrier for the nicotine.

Other examples of sources of cellulose include sugar beet fiber, cotton fiber, bran fiber, citrus pulp fiber, grass fiber, willow fiber, poplar fiber, bamboo fiber, and combinations thereof, or combinations thereof with wood pulp.

According to an advantageous embodiment of the invention said microcrystalline cellulose is added to the nicotine before being added to said gum base polymers.

The microcrystalline cellulose according to the above embodiment is carrier for the nicotine.

According to an advantageous embodiment of the invention said microcrystalline cellulose is added to said nicotine in the presence of a solvent or diluent, such as propylene glycol, water or ethanol.

According to an advantageous embodiment of the invention said diluent is dried off partly or fully before the composition comprising the microcrystalline cellulose and the nicotine is added to the gum base polymers.

The above mentioned average particles size may be especially relevant when providing the microcrystalline cellulose in the form of microcrystalline cellulose.

According to an advantageous embodiment of the invention said nicotine added to the microcrystalline cellulose is diluted so as to comprise at least 1% by weight of nicotine, such as between 2 and 75% by weight, such as between 5 and 25% by weight, such as between 10 and 15% by weight.

According to an advantageous embodiment of the invention the nicotine chewing gum has a tan (delta) of at less than 1.2, such as less than 1.1, such as less than 1.0.

According to an advantageous embodiment of the invention the nicotine chewing gum has a tan delta of at less than 1.2, such as less than 1.1, such as less than 1.0 wherein said tan (delta) is measured at an oscillation frequency of frequency of approximately 1 Hz.

According to an advantageous embodiment of the invention the nicotine chewing gum has a tan delta of at less than 1.2, such as less than 1.1, such as less than 1.0 wherein said tan (delta) is measured at an oscillation frequency of frequency of approximately 1 Hz and wherein said tan delta is measured at an oscillation torque of about 8 to 12 µN·m.

According to an advantageous embodiment of the invention the nicotine chewing gum has a tan delta of at less than 1.2, such as less than 1.1, such as less than 1.0 wherein said tan (delta) is measured at an oscillation frequency of frequency of approximately 1 Hz and wherein said tan delta is measured at an oscillation torque of about 8 to 12 µN·m and wherein said tan delta is measured by AR 1000 rheometer from TA Instruments and at a temperature of 37° C.

According to an advantageous embodiment of the invention the nicotine chewing gum has a tan delta of less than 1.2, such as less than 1.1, such as less than 1.0 wherein said tan (delta) is measured at an oscillation frequency of frequency of approximately 1 Hz and wherein said tan delta is measured at an oscillation torque which provides a linear viscoelastic response (LVR).

According to an advantageous embodiment of the invention the nicotine chewing gum has a tan delta of at less than 1.2, such as less than 1.1, such as less than 1.0 wherein said tan (delta) is measured at an oscillation frequency of frequency of approximately 1 Hz and wherein said tan delta is measured at an oscillation torque which provides a linear viscoelastic response (LVR) and wherein said tan delta is measured by AR 1000 rheometer from TA Instruments and at a temperature of 37° C.

According to an advantageous embodiment of the invention the tan (delta) is defined as (loss modulus G"/storage modulus G').

According to an advantageous embodiment of the invention the gum base polymers comprise natural gum base polymers in an amount less than 1% by weight, preferably less than 0.5% by weight, more preferably less than 0.2% by weight, most preferably less than 0.1% by weight.

According to an advantageous embodiment of the invention said chewing gum is a compressed chewing gum.

According to an advantageous embodiment of the invention said chewing gum comprises gum base granules, said gum base granules comprising gum base polymers.

According to an advantageous embodiment of the invention the gum base granules comprises further ingredients other than gum base polymers.

According to an advantageous embodiment of the invention the gum base granules have an average diameter below 2 millimeters, such as between 0.01 and 2 millimeters, such as between 0.1 and 2 millimeters.

According to an advantageous embodiment of the invention the gum base granules comprises gum base polymers in an amount of 0.1 to 99% by weight of the gum base granules.

According to an advantageous embodiment of the invention the nicotine chewing gum is a medical chewing gum.

The invention further relates to a method of producing a nicotine chewing gum, said method comprising the steps of
adding nicotine to microcrystalline cellulose to obtain a nicotine-microcrystalline cellulose mixture,
adding the nicotine-microcrystalline cellulose mixture to chewing gum mass,
forming a nicotine chewing gum from chewing gum mass with nicotine-microcrystalline cellulose mixture
wherein the nicotine chewing gum comprises gum base polymers, nicotine, and microcrystalline cellulose as a carrier for the nicotine,
the gum base polymers comprising polyvinyl acetate and vinyl laurate-vinyl acetate copolymer in an amount of more than 90% by weight, and
wherein the gum base polymers include 20-95% by weight of polyvinyl acetate and 5-80% by weight of vinyl laurate-vinyl acetate copolymer.

According to an advantageous embodiment of the invention the nicotine chewing gum contains no polyterpene resins and no resins based on gum rosin, wood rosin or tall oil resin.

According to an advantageous embodiment of the invention said nicotine is added to said microcrystalline cellulose in the form of free base nicotine, e.g. as diluted free base nicotine.

According to an advantageous embodiment of the invention the method according to any of its embodiments is adapted for producing a nicotine chewing gum according to any of its embodiments.

DEFINITIONS

Figure 1:
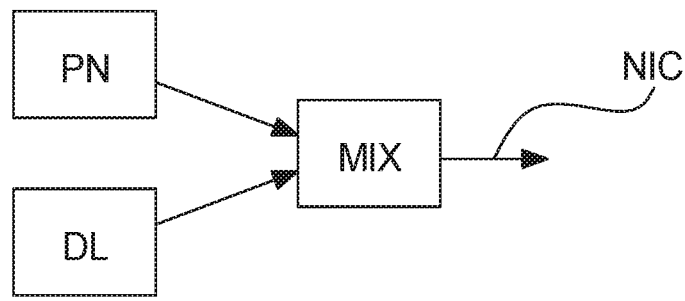
FIG. 1 illustrates a process for preparing a diluted nicotine liquid according to an embodiment of the invention.

The verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or an" thus usually means "at least one". Additionally, the words "a" and "an" when used in the present document in concert with the word comprising or containing denote "one or more."

As used herein, by the phrase "chewing gum" is meant any chewing gum such as extruded chewing gum, center-filled chewing gum, toffee-imitating chewing gum, or compressed chewing gum, slabs or sticks.

By the terms "gum base" and "gum base matrix" is meant the mainly water-insoluble and hydrophobic gum base ingredients that are mixed together, typically before the bulk portion of the chewing gum is added. The "gum base" may contain gum base polymers and plasticizers, waxes, emulsifiers, fats and/or fillers. The gum base may thus designate the typical water-insoluble chewing gum components, which may be manufactured in a first step and subsequently mixed with the mainly water soluble portion in a second step. The term gum base may, evidently, also refer to the relevant gum base components fed into an extruder and forming part of the final chewing gum when mixed with the chewing gum components in the extruder.

The term "bulk portion" intends to mean the mainly water-soluble and hydrophilic chewing gum ingredients that may be mixed into the gum base matrix, either in a separate process or in a one-step process by means of an extruder.

The term "gum base polymer" intends to mean resins and elastomers of polymeric origin and does not include, for example, plasticizers, waxes, emulsifiers, fats or fillers although these may also be present in a gum base.

The term "weight of the nicotine chewing gum", "weight of the chewing gum" or similar wording meaning the same is defined in the present context as weight of the nicotine chewing gum, not including the weight of an outer coating, such as a hard coating, soft coating, and the like.

By the phrase "texture" is meant a qualitative measure of the visco-elastic properties of the nicotine chewing gum and of the overall mouth-feel experienced by the user during the chewing process. Thus the term "texture" encompasses measurable quantities such as hardness and elasticity as well as more subjective parameters related to the chew-feel experienced by a user.

The term "natural resin", as used herein, means resinous compounds being either polyterpenes derived from terpenes of natural origin or resinous compounds derived from gum rosin, wood rosin or tall-oil rosin.

The term "synthetic polymer", as used herein, means polymers industrially synthesized by appropriate polymerization techniques.

The term "buffer", as used herein, refers to pH-control agents.

The term "free nicotine" is understood to include nicotine in its free base form, pure nicotine, and liquid nicotine.

The average particle size of cellulose is understood to mean the $D_{50}$ value as measured by laser diffraction analysis.

DETAILED DESCRIPTION OF THE INVENTION

In some embodiments of the invention, buffer may be added, to the nicotine chewing gum. In other embodiments, however, the nicotine chewing gum may be free of buffer.

Suitable buffers may be selected from the group consisting of tris buffers, amino acid buffers, carbonate, including bicarbonate or sesquicarbonate, glycerinate, phosphate, glycerophosphate, acetate, glyconate or citrate of an alkali metal, such as potassium and sodium, e.g. trisodium and tripotassium citrate, or ammonium, and mixtures thereof.

Buffer may be present in an amount of 0.5-10% by weight of the nicotine chewing gum.

A preferred buffer is sodium carbonate or a mixture of sodium carbonate and sodium bicarbonate.

Further suitable buffers may be selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Magnesium carbonate, Magnesium oxide, or any combination thereof.

The buffer may to some extent be microencapsulated or otherwise coated as granules with polymers and/or lipids being less soluble in saliva. Such microencapsulation controls the dissolution rate whereby the time frame of the buffering effect is extended.

However, in presently preferred embodiments an alkaline buffer is preferred, such as sodium carbonate and/or sodium hydrogen carbonate.

According to embodiments of the invention a preferred amount of gum base matrix in the final chewing gum is 30-75% by weight of the nicotine chewing gum before any optionally applied coating, such as 35-70% by weight of the nicotine chewing gum or 40-65% by weight of the nicotine chewing gum or 45-60% by weight of the nicotine chewing gum.

The formulation of gum bases can vary depending on the particular product to be prepared and on the desired masticatory and other sensory characteristics of the final product.

Besides the polyvinyl acetate and the vinyl laurate-vinyl acetate copolymer, the gum base may optionally contain further synthetic elastomers in an amount of less than 10% by weight of the gum base polymers such as less than 8% by weight of the gum base polymers or less than about 5% by weight of the gum base polymers.

Such synthetic elastomers may be selected from the group consisting of styrene-butadiene copolymers (SBR), polyisobutylene, isobutylene-isoprene copolymers (IIR also known as butyl rubber, BR), polyurethane and polyethylene.

Preferred synthetic elastomers are styrene-butadiene copolymers (SBR), polyisobutylene and isobutylene-isoprene copolymers (BR).

If non-tack chewing gum is desired, copolymers of methyl vinyl ether and maleic acid and derivatives thereof, such as Gantrez and/or copolymers of polyisoprene-graft maleic anhydride (PIP-g-MA) with polyethylene-glycol (PEG) or methoxy-polyethylene-glycol (MPEG) side chains, such as REV-7 provided by Revolymer, may be among the gum base polymers.

The gum base matrix may further comprise:
0 to 40% by weight waxes, 5 to 35% by weight softeners other than waxes, such as plasticizers, fats and emulsifiers, 0 to 50% by weight filler, and 0 to 5% by weight of miscellaneous ingredients such as antioxidants, colorants, etc.

According to an embodiment, natural resins are not used, or only in minute amounts. According to an embodiment of the invention the nicotine chewing gum is free of natural rosin esters, often referred to as ester gums including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the nicotine chewing gum comprises further chewing gum ingredients selected from the group consisting of flavors, dry-binders, tableting aids, anti-caking agents, emulsifiers, antioxidants, enhancers, absorption enhancers, high intensity sweeteners, softeners, colors, active ingredients, water-soluble indigestible polysaccharides, water-insoluble polysaccharides or any combination thereof.

According to embodiments of the invention, said emulsifiers are selected from the group of cyclodextrins, polyoxyethylene castor oil derivatives, polyoxyethylene alkyl ethers, macrogol alkyl ethers, block copolymers of ethylene and propylene oxides, polyoxyethylene alkyl ethers, polyoxyethylene glycols, polyoxyethylene sorbitan fatty acid esters, polyoxyethylene (20) sorbitan monostearates, polyoxyethylene (20) sorbitan monooleates, polyoxyethylene stearates, sorbitan esters, diacetyl tartaric ester of monoglycerides, lactylated monoglycerides, mono- and/or di-glycerides of fatty acids such as glycerol monostearate, Acetem, lecithines or any combination thereof.

In an embodiment of the invention, said chewing gum comprises emulsifiers in an amount in the range of 0.1% to 25% by weight of said chewing gum.

In an embodiment of the invention the nicotine chewing gum comprises flavor. Flavor may typically be present in amounts between 0.01 and 10% by weight of the nicotine chewing gum, such as between 0.01 and 5% by weight of the nicotine chewing gum.

Non-exhaustive examples of flavors suitable in embodiments of the present invention are coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, *eucalyptus*, and mint, fruit essence such as from apple, pear, peach, strawberry, apricot, raspberry, cherry, pineapple, and plum essence. The essential oils include peppermint, spearmint, menthol, *eucalyptus*, clove oil, bay oil, anise, thyme, cedar leaf oil, nutmeg, and oils of the fruits mentioned above.

Petroleum waxes aid in the curing of the finished gum made from the gum base as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavors escape from this wax versus a wax having larger crystal sizes.

Petroleum wax (refined paraffin and microcrystalline wax) and paraffin wax are composed of mainly straight-chained normal-alkanes and branched iso-alkanes. The ratio of normal-alkanes to iso-alkanes varies.

The normal-alkanic waxes typically have carbon chain lengths >0-18 but the lengths are not predominantly longer than C-30. The branched and ring structures are located near the end of the chain for those waxes that are predominantly normal-alkanic. The viscosity of normal-alkanic waxes is <10 mm2/s (at 100° C.) and the combined number average molecular weight is <600 g/mole.

The iso-alkanic waxes typically have carbon lengths that are predominantly greater than C-30. The branched chains and ring structures are located randomly along the carbon chain in those waxes that are predominantly iso-alkanic. The viscosity of iso-alkanic waxes is greater than 10 mm2/s (at 100° C.) and the combined number average molecular weight is >600 g/mole.

Synthetic waxes are produced by means that are atypical for petroleum wax production and are thus not considered petroleum wax. The synthetic waxes may include waxes containing branched alkanes and copolymerized with monomers such as, but not limited to propylene, polyethylene, and Fischer Tropsch type waxes. Polyethylene wax is a synthetic wax containing alkane units of varying lengths having attached thereto ethylene monomers.

Waxes and fats are conventionally used for the adjustment of the texture and for softening of the chewing gum base when preparing chewing gum bases. In connection with the present invention, any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

Suitable vegetable oils include but are not limited to oils that are based on coconut, palm, palm kernel, cotton seed, rape seed or sunflower and combinations thereof Antioxidants prolong shelf life and storage of gum base, finished gum or their respective components including fats and flavor oils.

Antioxidants suitable for use in gum base include butylated hydroxyanisole (BHA), butylated hydroxytoluene (BHT), betacarotenes, tocopherols, acidulants such as Vitamin C, propyl gallate, other synthetic and natural types or mixtures thereof.

In some embodiments, one or more colors can be included in the nicotine chewing gum.

According to an embodiment, the nicotine is in free base form.

In an embodiment of the invention, said nicotine salts are selected from the group comprising nicotine hydrochloride, nicotine dihydrochloride, nicotine monotartrate, nicotine bitartrate, nicotine sulfate, nicotine zinc chloride, nicotine salicylate, or any combination thereof.

High intensity artificial sweetening agents can also be used according to preferred embodiments of the invention. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside and the like, alone or in combination.

In order to provide longer lasting sweetness and flavor perception, it may be desirable to encapsulate or otherwise control the release of at least a portion of the artificial sweeteners.

Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another chewing gum component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the nicotine chewing gum.

A nicotine chewing gum and/or gum base may, if desired, include one or more fillers/texturizers including as examples, magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, and combinations thereof.

According to an embodiment of the invention, one preferred filler/texturizer is calcium carbonate.

A number of chewing gum components well known within the art may be applied within the scope of the present invention. Such components comprise but are not limited to waxes, fats, softeners, fillers, bulk sweeteners, flavors, antioxidants, emulsifiers, coloring agents, binding agents and acidulants.

In an embodiment of the invention, the nicotine chewing gum is provided with an outer coating selected from the group consisting of hard coating, soft coating and edible film-coating or any combination thereof.

Microcrystalline cellulose (MCC) may be prepared e.g. by hydrolyzing wood pulp by means of mineral acid. Thereby, microcrystalline cellulose may be obtained as purified, practically depolymerized cellulose. In more detail the manufacturing may typically comprise starting from selected rolls of wood pulp that are diced, or cut, into small particles. The chopped particles may then be hydrolyzed under heat and pressure by mineral acid. Thereafter, the obtained mixture may be washed and filtered.

Also, spray drying may be employed, which can be used to control the particle size distribution and the moisture content.

In some embodiments, microcrystalline cellulose may be obtained from other sources, such as other plant sources. Microcrystalline cellulose with different moisture content may be used. Typical moisture content may for example be about 5%, although other moisture contents, such as e.g. 3% or 1.5%, are also known to work.

Microcrystalline cellulose is commercially available, and may for example be obtained from FMC Biopolymer, e.g. the products known as Avicel PH 101, PH 102, PH 103, PH 105, PH 112, PH 113, PH 200, PH 301, and PH 302.

The nicotine chewing gum of the invention may be manufactured as an extruded chewing gum, or as a compressed chewing gum.

The chewing gum may be produced by a conventional batch or extrusion process. The process is well-known in the art. It should be noted that the temperature under which the nicotine is added may advantageously be relatively low, e.g. be lower than 50 degrees Celsius.

When manufacturing a compressed chewing gum tablet a method is applied, which is basically very different than the extruded chewing gum, but may broadly be described as an initial conventional mixing of the gum base, followed by a granulation of the obtained gum base mix. The obtained gum base granules may then be mixed with further chewing gum ingredients, such as sweeteners and flavor. This final granule mix may then be compressed under high pressure into a chewing gum tablet. For each compression a layer is made and in this way it is possible to make multi-layered chewing gums, such as two, three or four layers, wherein each layer may include an individual composition, e.g. nicotine or different colors may be used for visual purposes, etc.

The nicotine may advantageously be applied in a gum base-containing module or a tablet-module substantially free of gum base. In cases where a high initial release of nicotine is desired, the nicotine may advantageously be comprised in a tablet module substantially free of gum base whereas e.g. flavors and/or sweeteners advantageously may be added to the gum base-containing module and very often to both types of modules. The flavors and/or sweeteners may both be added as separate particles which are mixed and compressed with gum base-containing particles in one module and it may be incorporated into gum base-containing granules.

Referring to FIG. 1, a process for preparing a diluted nicotine liquid NIC according to an embodiment of the invention is illustrated.

Pure nicotine PN is added to a mixer MIX together with a diluent DL. The diluent may for example be or comprise water, ethanol or propylene glycol.

The ratio between the diluent and the nicotine may in some cases be around a 20% solution, i.e. comprising 20 percent by weight of nicotine, the remaining 80 percent being diluent. However, generally, the nicotine content may be within the range of between 2 and 75% by weight.

After mixing for an effective period of time, a nicotine liquid NIC is obtained, which is a mixture of the pure nicotine PN and the diluent DL.

Figure 2:
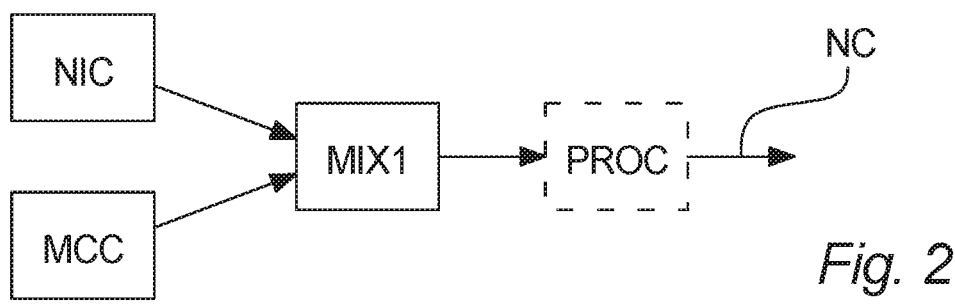
FIG. 2 illustrates a process for preparing a nicotine-microcrystalline cellulose mixture according to an embodiment of the invention.

Referring to FIG. 2, a process for preparing a nicotine-microcrystalline cellulose mixture according to an embodiment of the invention is illustrated.

First a nicotine liquid NIC is added to a mixer MIX1 together with microcrystalline cellulose MCC. The mixing ratio between the nicotine liquid NIC and the microcrystalline cellulose may in some cases be around 1:1, but may generally vary from about 1:1000 to about 1:1.

The nicotine liquid NIC may in some embodiments be pure nicotine, and may in other embodiments be diluted nicotine. Diluted nicotine may often be simpler to handle. Examples of diluents used to dilute nicotine may include water, ethanol, propylene glycol, and other diluents. The nicotine liquid NIC as diluted nicotine may be obtained by means of the process illustrated in connection with FIG. 1.

The mixer MIX1 may be any type of mixer capable of mixing the nicotine liquid NIC and the microcrystalline cellulose MCC.

The mixer MIX1 is operated until an effective mixing of the nicotine liquid NIC and the microcrystalline cellulose MCC is obtained.

Thereafter the resulting mixture of the nicotine liquid NIC and the microcrystalline cellulose MCC may in some cases be subjected to a further processing PROC. This processing PROC may involve letting the mixture of the nicotine liquid NIC and the microcrystalline cellulose MCC rest or soak for a period of time, e.g. in a sealed container, i.e. equilibrating the nicotine liquid NIC and the microcrystalline cellulose MCC.

In some cases further mixing, either by means of mixer MIX1 or another mixer, may be employed.

In some cases the processing PROC may be carried out in the mixer MIX1, whereas in other cases the processing is carried out in separate process equipment. It may in some cases be especially advantageous to perform the processing PROC in the mixer MIX1 when further mixing is performed.

The final nicotine-microcrystalline cellulose mixture may be obtained from the processing PROC, if used, or from the mixer MIX1 if the processing PROC is not used.

Figure 3:
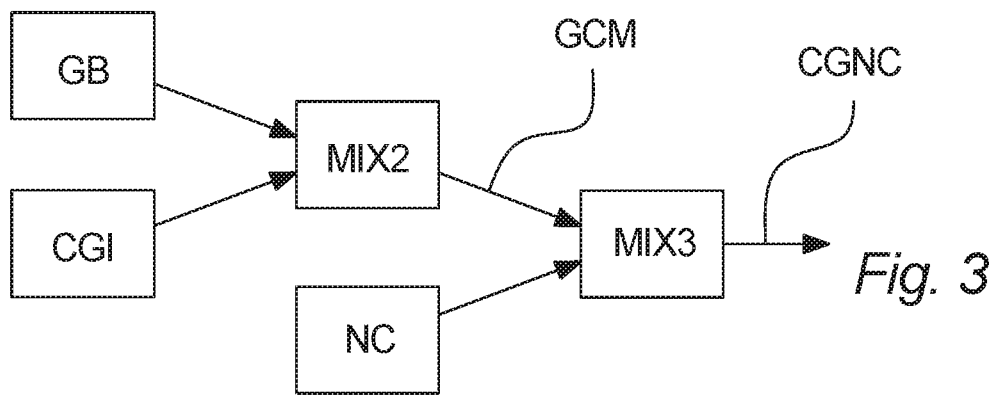
FIG. 3 illustrates a process for preparing a chewing gum mass comprising nicotine-MCC mixture according to an embodiment of the invention.

Referring to FIG. 3, a process for preparing chewing gum with nicotine-microcrystalline cellulose GBNC according to an embodiment of the invention is illustrated.

Nicotine-microcrystalline cellulose mixture NC obtained in accordance with the embodiment illustrated on FIG. 2 may be used.

First, chewing gum ingredients CGI, including e.g. filler, is added to a mixer MIX2 together with a gum base GB and mixed therein to obtain a chewing gum mass CGM as a mixture of gum base and chewing gum ingredients GCI. The gum base must comprise an effective amount of gum base polymers. It is very important that the gum base is chosen such that the gum base polymers comprise polyvinyl acetate and vinyl laurate-vinyl acetate copolymer in an amount of more than 90% by weight of the gum base polymers. Similarly, the gum base should also be chosen such that the gum base polymers include 20-95% by weight of polyvinyl acetate and 5-80% by weight of vinyl laurate-vinyl acetate copolymer.

Then, the nicotine-microcrystalline cellulose mixture NC is added to a mixer MIX3 together with the chewing gum mass CGM. Thereby, a chewing gum mass with nicotine-microcrystalline cellulose CGNC is obtained.

In some embodiments, the mixers MIX2 and MIX3 are different mixers, whereas in other embodiments they are the same mixer, but where timing divides the use of the mixer into two separate actions, first the mixing of the gum base GB with the chewing gum ingredients CGI, then mixing with the nicotine-MCC mixture NC.

The obtained chewing gum mass with nicotine-microcrystalline cellulose CGNC may be used to produce chewing gums. In some embodiments further ingredients are added, e.g. sweeteners, flavors, further fillers etc. In other embodiments, such further ingredients, if needed, are added in a different order, according to the specific situation.

The nicotine chewing gum produced from the chewing gum mass with nicotine-microcrystalline cellulose CGNC may be compressed chewing gum or extruded chewing gum.

When using nicotine liquid NIC comprising a diluent DL, e.g. as described in relation to FIG. 1, the composition of the nicotine chewing gum should be adjusted thereto, if needed. For example, when using propylene glycol as a diluent, the propylene glycol may act as a plasticizer in the chewing gum composition, and, as a result thereof, the amount of other plasticizers may often have to be reduced.

In some cases the diluent may be dried off or partially dried off from the nicotine-MCC mixture NC. Thereby, the need for adjusting the chewing gum composition to the amount of diluent may be reduced or eliminated.

As illustrated in connection with FIGS. 1-3, MCC and liquid nicotine are mixed and equilibrated. The cellulosic fiber and liquid nicotine can be mixed in a suitable mixing device for any suitable length of time. In some cases, the cellulosic fiber and liquid nicotine can be mixed with a mixing implement rotating at a speed of less than 500 rpm, less than 250 rpm, less than 150 rpm, less than 100 rpm, less than 60 rpm, less than 30 rpm, or less than 10 rpm. For example, the mixer can be a Kitchenaid, Hobart Mixer, ribbon blender, or other mixing apparatus depending on the desired batch size. In some cases, the MCC and liquid nicotine can be mixed using a rotating and/or vibrating drum. In some cases, the cellulosic fibers and liquid nicotine can be mixed for at least 1 minute, at least 3 minutes, at least 5 minutes, at least 10 minutes, or at 4 least 30 minutes prior to incorporating a resulting MCC-nicotine mixture into a chewing gum formulation or gum base formulation.

After mixing cellulosic fiber and liquid nicotine, the cellulosic fiber-nicotine mixture can be equilibrated in a sealed container. In some cases, the sealed container can be a bag (e.g. a poly bag). In some cases, the MCC-nicotine mixture can be equilibrated for at least 30 minutes, at least 1 hour, at least 2 hours, at least 4 hours, at least 6 hours, at least 8 hours, or at least 10 hours prior to use or incorporation into an oral product. In some cases, a MCC-nicotine mixture can be further mixed or agitated during the equilibrating process. For example, a cellulosic fiber-nicotine mixture equilibrating in a poly bag can be agitated during the equilibrating process at a select time (e.g., 2 hours into the equilibrating process).

The following non-limiting examples illustrate different variations of the present invention. The examples are meant for indicating the inventive concept; hence the mentioned examples should not be understood as exhaustive for the present invention.

EXAMPLES

Example 1

Preparation of Nicotine MCC Premix

A nicotine-microcrystalline cellulose (MCC) premix is made by first adding free nicotine to propylene glycol (PG) to obtain a 20% solution of nicotine in propylene glycol. Then, 50 grams of the nicotine-propylene glycol solution is added to 50 gram of microcrystalline cellulose provided as Avicel PH 102 from FMC Biopolymer. This is then mixed in a Kitchenaid mixer operated at about 30 RPM for about 30 minutes at room temperature. Finally, the obtained mixture of the nicotine-propylene glycol solution and the microcrystalline cellulose is equilibrated for about 60 minutes in a sealed container.

Example 2

Preparation of Nicotine MCC Premix

A nicotine-MCC premix is made by adding first adding free nicotine to propylene glycol (PG) to obtain a 10% solution of nicotine in propylene glycol. Then, 50 grams of the nicotine-propylene glycol solution is added to 50 gram of microcrystalline cellulose provided as Avicel PH 102 from FMC Biopolymer. The nicotine-propylene glycol solution and the microcrystalline cellulose are then mixed in a Kitchenaid mixer operated at about 30 RPM for about 30 minutes at room temperature. Finally, the obtained mixture of the nicotine-propylene glycol solution and the microcrystalline cellulose is equilibrated for about 60 minutes in a sealed container.

Example 3

Preparation of Nicotine MCC Premix

A nicotine-MCC premix is made by adding first adding free nicotine to propylene glycol (PG) to obtain a 20% solution of nicotine in propylene glycol. Then, 50 grams of the nicotine-propylene glycol solution is added to 50 gram of microcrystalline cellulose provided as Avicel PH 101 from FMC Biopolymer. The nicotine-propylene glycol solution and the microcrystalline cellulose are then mixed in a Kitchenaid mixer operated at about 30 RPM for about 30 minutes at room temperature. Finally, the obtained mixture of the nicotine-propylene glycol solution and the microcrystalline cellulose is equilibrated for about 60 minutes in a sealed container.

Example 4

Preparation of Gum Bases

Ten different gum bases (GB), given GB numbers 101-110, were prepared by the following process: The polymers polyvinyl acetate (PVA), vinyl acetate-vinyl laurate copolymer (VA-VL), and optionally polyisobutylene (PIB) are mixed at 120° C. together with filler, here calcium carbonate or talc, in a mixer having horizontally placed Z-shaped arms for mixing.

When the polymers are softened, triacetin is added, followed by addition of emulsifier, wax and vegetable fat.

After a total mixing time of about 45-60 minutes, the mixture is discharged into a pan and allowed to cool to room temperature.

In case of example VIII, GB 108, comparative (comp.) example IX, GB 109, and standard (Std.) gum base example X, GB 110, which include butyl rubber (BR), BR is added in the initial mixing step, and the mixing time is extended to a total of about 90-105 minutes.

In case of comparative (comp.) example IX, GB 109, the natural resin is added before the addition of triacetin, and in case of standard (Std.) example X, GB 110, the natural resin is added after about 30 minutes before the addition of softeners.

The gum base compositions were as displayed in table 1A and 1B, the amounts given corresponding to percentages by weight of the gum base:

TABLE 1A

Gum base compositions, VA-VL I = vinyl acetate-vinyl laurate copolymer (Vinnapas B 500/40VL, supplied by Wacker); VA-VL II = vinyl acetate-vinyl laurate copolymer (Vinnapas B 500/20VL, supplied by Wacker); PVA I = polyvinyl acetate (Vinnapas B 1.5 sp, supplied by Wacker); PVA II = polyvinyl acetate (Vinnapas B 30 sp, supplied by Wacker); PIB = polyisobutylene (Oppanol B12, supplied by BASF); BR = butyl rubber (isobutylene-isoprene copolymer); Nat. resin = glycerol ester of hydrogenated gum rosin; Veg. fat = vegetable fat.

| | Raw material | | | | |
|---|---|---|---|---|---|
| GB no. | Ex. I 101 | Ex. II 102 | Ex. III 103 | Ex. IV 104 | Ex. V 105 |
| VA-VL I | 20 | — | 14 | — | 22 |
| VA-VL II | — | 20 | — | 22 | — |
| PVA I | 32 | 33 | 18 | 35 | 33 |
| PVA II | — | — | 5.0 | — | — |
| PIB | — | — | — | — | — |
| BR | — | — | — | — | — |
| Nat. Resin | — | — | — | — | — |
| Calcium Carbonate | — | 19 | — | 22 | 17 |
| Talc | 20 | — | 41 | — | — |
| Triacetin | 8 | 8 | 6 | 7 | 2 |
| Emulsifier | 5 | 7 | 3 | 8 | 9 |
| Wax, micro-crystalline | 13 | 13 | 10 | — | 12 |
| Veg. fat | 2 | — | 3 | 6 | 5 |
| Total | 100 | 100 | 100 | 100 | 100 |

TABLE 1B

Gum base compositions, VA-VL I = vinyl acetate-vinyl laurate copolymer (Vinnapas B 500/40VL, supplied by Wacker); VA-VL II = vinyl acetate-vinyl laurate copolymer (Vinnapas B 500/20VL, supplied by Wacker); PVA I = polyvinyl acetate (Vinnapas B 1.5 sp, supplied by Wacker); PVA II = polyvinyl acetate (Vinnapas B 30 sp, supplied by Wacker); PIB = polyisobutylene (Oppanol B12, supplied by BASF); BR = butyl rubber (isobutylene-isoprene copolymer); Nat. resin = glycerol ester of hydrogenated gum rosin; Veg. fat = vegetable fat.

| | Raw material | | | | |
|---|---|---|---|---|---|
| GB no. | Ex. VI 106 | Ex. VII 107 | Ex. VIII 108 | Ex. IX comp. 109 | Ex. X Std. 110 |
| VA-VL I | 21 | 20 | 20 | 10 | — |
| VA-VL II | — | — | — | — | — |
| PVA I | 31 | 30 | 30 | 20 | 25 |
| PVA II | — | — | — | — | — |
| PIB | 3.0 | 5.0 | 3.0 | 3.0 | 5 |
| BR | — | — | 2.0 | 2.0 | 5 |
| Nat. resin | — | — | — | 20 | 25 |
| Calcium Carbonate | 17 | 17 | 17 | 17 | 17 |
| Talc | — | — | — | — | — |
| Triacetin | 2 | 2 | 2 | 2 | — |
| Emulsifier | 9 | 9 | 9 | 9 | 5 |
| Wax, micro-crystalline | 12 | 12 | 12 | 12 | 13 |
| Veg. fat | 5 | 5 | 5 | 5 | 5 |
| Total | 100 | 100 | 100 | 100 | 100 |

Example 5

Preparation of Nicotine Chewing Gum

Nicotine chewing gum (NCG), given NCG numbers 1001-1010, using gum bases nos. 101-110 from Table 1, respectively, were prepared as follows:

Gum base and filler are mixed in a mixer having horizontally placed Z-shaped arms for mixing. The mixer was preheated to a temperature of up to approximately 50° C.

When the content of the mixer is homogeneous, the other ingredients are added according to a specified time schedule. Nicotine is added as a nicotine-MCC premix (as disclosed in Example 1).

The chewing gum compositions were as displayed in table 2A and 2B, the amounts given corresponding to percentages by weight of the nicotine chewing gum:

TABLE 2A

Nicotine chewing gum compositions; MCC = microcrystalline cellulose. Liquid sweetener may for example be lycasin. Intense sweetener may for example be sucralose. Flavor may for example be pepper-mint flavor.

| | Raw material | | | | |
|---|---|---|---|---|---|
| NCG no. | Ex. XI 1001 | Ex. XII 1002 | Ex. XIII 1003 | Ex. XIV 1004 | Ex. XV 1005 |
| GB 101 | 52 | — | — | — | — |
| GB 102 | — | 52 | — | — | — |
| GB 103 | — | — | 52 | — | — |
| GB 104 | — | — | — | 52 | — |
| GB 105 | — | — | — | — | 52 |
| GB 106 | — | — | — | — | — |
| GB 107 | — | — | — | — | — |
| GB 108 | — | — | — | — | — |
| GB 109 | — | — | — | — | — |
| GB 110 | — | — | — | — | — |
| Filler | 19 | 19 | 19 | 19 | 19 |
| Nicotine-MCC premix | 2.0 | 2.0 | 2.0 | 2.0 | 2.0 |
| Sodium hydrogen carbonate | 1.0 | 1.0 | 1.0 | 1.0 | 1.0 |
| Sodium carbonate | 2.0 | 2.0 | 2.0 | 2.0 | 2.0 |
| Sorbitol powder | 18 | 18 | 18 | 18 | 18 |
| Liquid sweetener | 1.5 | 1.5 | 1.5 | 1.5 | 1.5 |
| Intense sweetener | 0.4 | 0.4 | 0.4 | 0.4 | 0.4 |
| Flavor | 4.1 | 4.1 | 4.1 | 4.1 | 4.1 |
| Total | 100 | 100 | 100 | 100 | 100 |

TABLE 2B

Nicotine chewing gum compositions; MCC = microcrystalline cellulose. Liquid sweetener may for example be lycasin. Intense sweetener may for example be sucralose. Flavor may for example be pepper-mint flavor.

| | Raw material | | | | |
|---|---|---|---|---|---|
| NCG no. | Ex. XVI 1006 | Ex. XVII 1007 | Ex. XVIII 1008 | Ex. XIX Comp. 1009 | Ex. XX Std. 1010 |
| GB 101 | — | — | — | — | — |
| GB 102 | — | — | — | — | — |
| GB 103 | — | — | — | — | — |
| GB 104 | — | — | — | — | — |
| GB 105 | — | — | — | — | — |
| GB 106 | 52 | — | — | — | — |
| GB 107 | — | 52 | — | — | — |
| GB 108 | — | — | 52 | — | — |
| GB 109 | — | — | — | 52 | — |
| GB 110 | — | — | — | — | 52 |
| Filler | 19 | 19 | 19 | 19 | 19 |

TABLE 2B-continued

Nicotine chewing gum compositions; MCC = microcrystalline cellulose. Liquid sweetener may for example be lycasin. Intense sweetener may for example be sucralose. Flavor may for example be pepper-mint flavor.

| NCG no. | Raw material | | | | |
|---|---|---|---|---|---|
| | Ex. XVI 1006 | Ex. XVII 1007 | Ex. XVIII 1008 | Ex. XIX Comp. 1009 | Ex. XX Std. 1010 |
| Nicotine-MCC premix | 2.0 | 2.0 | 2.0 | 2.0 | 2.0 |
| Sodium hydrogen carbonate | 1.0 | 1.0 | 1.0 | 1.0 | 1.0 |
| Sodium carbonate | 2.0 | 2.0 | 2.0 | 2.0 | 2.0 |
| Sorbitol powder | 18 | 18 | 18 | 18 | 18 |
| Liquid sweetener | 1.5 | 1.5 | 1.5 | 1.5 | 1.5 |
| Intense sweetener | 0.4 | 0.4 | 0.4 | 0.4 | 0.4 |
| Flavor | 4.1 | 4.1 | 4.1 | 4.1 | 4.1 |
| Total | 100 | 100 | 100 | 100 | 100 |

Example 6

Evaluation of Nicotine Chewing Gum

Different examples of the nicotine chewing gum were evaluated with respect to texture, release of flavor and nicotine, taste profile and other important features.

The nicotine chewing gum is highly suitable as delivery vehicle for nicotine.

LIST OF FIGURE REFERENCES

NIC. Nicotine liquid
MCC. Microcrystalline cellulose
MIX. Mixer
MIX1. Mixer
MIX2. Mixer
MIX3. Mixer
PROC. Processing
GB. Gum base
NC. Nicotine-microcrystalline cellulose mixture
CGNC. Chewing gum mass with nicotine-microcrystalline cellulose mixture
PN. Pure nicotine
DL. Diluent
CGM. Chewing gum mass
CGI. Chewing gum ingredients

The invention claimed is:

1. A nicotine chewing gum comprising gum base polymers, nicotine, and microcrystalline cellulose as a carrier for the nicotine,
   the gum base polymers comprising polyvinyl acetate and vinyl laurate-vinyl acetate copolymer in an amount of more than 90% by weight of the gum base polymers, and
   wherein the gum base polymers include 20-95% by weight of polyvinyl acetate and 5-80% by weight of vinyl laurate-vinyl acetate copolymer.

2. The nicotine chewing gum according to claim 1, wherein said nicotine is nicotine in its base form.

3. The nicotine chewing gum according to claim 1, wherein a total content of gum base ingredients selected from the group consisting of polyterpene resins, resins based on gum rosin, wood rosin and tall oil resin is less than 5 percent by weight of the nicotine chewing gum.

4. The nicotine chewing gum according to claim 1, wherein the nicotine chewing gum contains no polyterpene resins and no resins based on gum rosin, wood rosin or tall oil resin.

5. The nicotine chewing gum according to claim 1, wherein the nicotine chewing gum comprises gum base polymers in an amount of between 15 and 80 percent by weight of the nicotine chewing gum.

6. The nicotine chewing gum according to claim 1, wherein said microcrystalline cellulose is provided in the form of particles having an average particle size between 10 and 250 micrometers.

7. The nicotine chewing gum according to claim 1, wherein the nicotine chewing gum comprises buffer.

8. The nicotine chewing gum according to claim 7, wherein the buffer is present in an amount of 0.5 to 5% by weight of the nicotine chewing gum.

9. The nicotine chewing gum according to claim 1, wherein the nicotine chewing gum is free of ion-exchange resins.

10. The nicotine chewing gum according to claim 1, wherein said chewing gum comprises one or more further active ingredients.

11. The nicotine chewing gum according to claim 1, wherein said chewing gum comprises one or more fillers, wherein the filler is present in an amount of 5-45% by weight of the nicotine chewing gum.

12. The nicotine chewing gum according to claim 1, wherein the gum base polymers consist of synthetic gum base polymers.

13. The nicotine chewing gum according to claim 1, wherein a weight ratio between the polyvinyl acetate and the vinyl laurate-vinyl acetate copolymer is from 8:1 to 2:3.

14. The nicotine chewing gum according to claim 1, wherein a weight ratio between vinyl acetate monomers of vinyl laurate-vinyl acetate copolymer and vinyl laurate monomers of vinyl laurate-vinyl acetate copolymer is less than 90:10.

15. The nicotine chewing gum according to claim 1, wherein the polyvinyl acetate has a weight-average molecular weight Mw of from 5,000 to 120,000 g/mol.

16. The nicotine chewing gum according to claim 1, wherein the vinyl acetate-vinyl laurate copolymer has a weight-average molecular weight Mw of from 80,000 to 700,000 g/mol.

17. The nicotine chewing gum according to claim 1, wherein synthetic gum base polymers are forming part of the gum base, wherein the gum base comprises 15-45% by weight of polyvinyl acetate, 10-30% by weight of vinyl laurate-vinyl acetate copolymers, 15-45% by weight of fillers, 5-30% by weight of waxes or fats, 1-10% by weight of plasticizers and 1-10% by weight of emulsifiers.

18. The nicotine chewing gum according to claim 1, wherein the nicotine chewing gum comprises bulk sweetener in an amount of 5 to about 95% by weight of the nicotine chewing gum.

19. The nicotine chewing gum according to claim 1, wherein said microcrystalline cellulose is provided in the form of particles having an average particle size between 15 and 200 micrometers.

20. The nicotine chewing gum according to claim 1, wherein said microcrystalline cellulose has a specific surface area of between 0.65 and 1.5 $m^2/g$.

21. A method of producing a nicotine chewing gum, said method comprising the steps of
   adding nicotine to microcrystalline cellulose to obtain a nicotine-microcrystalline cellulose mixture, adding the nicotine-microcrystalline cellulose mixture to chewing gum mass, wherein the nicotine chewing gum comprises gum base polymers, nicotine, and microcrystalline cellulose as a carrier for the nicotine, the gum base polymers comprising polyvinyl acetate and vinyl laurate-vinyl acetate copolymer in an amount of more than 90% by weight, and wherein the gum base polymers include 20-95% by weight of polyvinyl acetate and 5-80% by weight of vinyl laurate-vinyl acetate copolymer.

* * * * *